US009516855B2

(12) United States Patent
Rosen

(10) Patent No.: US 9,516,855 B2
(45) Date of Patent: Dec. 13, 2016

(54) METHOD AND ARRANGEMENTS FOR IMPROVING ANIMAL'S PERFORMANCE BY REDUCING THE AMOUNT OF BIOLOGICALLY ACTIVE PARTICLES IN THE STABLE AIR

(71) Applicant: Karl G Rosen, Kungalv (SE)

(72) Inventor: Karl G Rosen, Kungalv (SE)

(73) Assignee: NEOVENTOR MEDICINSK INNOVATION AB, Kungalv (SE)

( * ) Notice: Subject to any disclaimer, the term of this patent is extended or adjusted under 35 U.S.C. 154(b) by 189 days.

(21) Appl. No.: 14/352,895

(22) PCT Filed: Dec. 14, 2012

(86) PCT No.: PCT/SE2012/000201
§ 371 (c)(1),
(2) Date: Apr. 18, 2014

(87) PCT Pub. No.: WO2013/089610
PCT Pub. Date: Jun. 20, 2013

(65) Prior Publication Data
US 2014/0245886 A1    Sep. 4, 2014

(30) Foreign Application Priority Data
Dec. 14, 2011    (SE) .................................... 1130120

(51) Int. Cl.
*A01K 1/00*    (2006.01)
*B03C 3/41*    (2006.01)
(Continued)

(52) U.S. Cl.
CPC .............. *A01K 1/0047* (2013.01); *A61L 9/22* (2013.01); *B03C 3/41* (2013.01); *H01T 23/00* (2013.01); *B03C 2201/10* (2013.01)

(58) Field of Classification Search
CPC combination set(s) only.
See application file for complete search history.

(56) References Cited

U.S. PATENT DOCUMENTS 4,152,183 A * 5/1979 Honacker ................. B03C 3/49
138/109
5,296,019 A * 3/1994 Oakley ..................... B03C 3/41
361/226

(Continued)

FOREIGN PATENT DOCUMENTS

GB    2090547 A    *    7/1982    ............... B03C 3/40
GB    2304576 A        3/1997

(Continued)

OTHER PUBLICATIONS

International Search Report, dated Mar. 26, 2013, from corresponding PCT application.

*Primary Examiner* — Duane Smith
*Assistant Examiner* — Sonji Turner
(74) *Attorney, Agent, or Firm* — Young & Thompson

(57) ABSTRACT

A method and arrangement to improve animal's biological and/or physical performance by reducing the bioload, defined as biologically active particles in the stable air or within transporter vehicles. The method includes generating a negatively charged electrostatic field operating within the room capturing the particles. The arrangement includes elements for producing a negatively charged electrostatic field capturing air borne particulate matter whereby high voltage >6 kV at low amperage (<10 mA) is applied to a basic conductive structure positioned in the air of the stable or the transporter vehicle, to which carbon fiber filaments are attached, causing the release of electrons from the free ending carbon fibers into the air and thereby generating the negatively charged electrostatic field.

7 Claims, 2 Drawing Sheets

(51) Int. Cl.
    *A61L 9/22*           (2006.01)
    *H01T 23/00*       (2006.01)

(56) References Cited

U.S. PATENT DOCUMENTS

| | | | | |
|---|---|---|---|---|
| 5,792,243 | A * | 8/1998 | Meffert | B03C 3/64 |
| | | | | 313/355 |
| 6,735,830 | B1 | 5/2004 | Mercier | |
| 7,161,789 | B2 * | 1/2007 | Robertson | B03C 3/383 |
| | | | | 361/230 |
| 7,976,616 | B2 * | 7/2011 | Alam | B03C 3/41 |
| | | | | 313/351 |
| 8,460,430 | B2 * | 6/2013 | Baumgartner | B03C 3/12 |
| | | | | 119/437 |
| 8,690,989 | B2 * | 4/2014 | Baumgartner | B03C 3/12 |
| | | | | 119/437 |
| 9,114,404 | B2 * | 8/2015 | Alam | B03C 3/41 |
| 2003/0231459 | A1 | 12/2003 | Robertson | |
| 2008/0190296 | A1 * | 8/2008 | Alam | B03C 3/41 |
| | | | | 96/83 |
| 2010/0269691 | A1 * | 10/2010 | Baumgartner | B03C 3/12 |
| | | | | 95/6 |
| 2011/0308384 | A1 * | 12/2011 | Baumgartner | B03C 3/12 |
| | | | | 95/6 |

FOREIGN PATENT DOCUMENTS

| | | | |
|---|---|---|---|
| GB | 2462250 | A | 2/2010 |
| JP | 9172907 | A | 7/1997 |
| JP | 2000014265 | A | 1/2000 |
| JP | 2004215535 | A | 8/2004 |
| KR | 20020092602 | A | 12/2002 |

* cited by examiner

METHOD AND ARRANGEMENTS FOR IMPROVING ANIMAL'S PERFORMANCE BY REDUCING THE AMOUNT OF BIOLOGICALLY ACTIVE PARTICLES IN THE STABLE AIR

FIELD OF THE INVENTION

The present invention relates generally to a technique used in housing of animals that are required to convert feed into desirable results with high efficiency and performance. More particularly, it relates to a method of improving the animal's performance such as physical capacity, growth or the efficiency of the animals to convert its feed into desirable products (e.g. eggs, milk and muscles) and arrangements for use of said method.

BACKGROUND

Animals must balance their energy budget despite seasonal changes in both energy availability and physiological expenditures. Immunity, in addition to growth, thermoregulation, and cellular maintenance, requires substantial energy to maintain function. Mounting an immune response requires significant energy and therefore requires using resources that could otherwise be allocated to other physiological processes. Energetic trade-offs are likely when energy demands are high. Obviously, faster growth or a more efficient conversion of feed into desirable products in an animal is both economically and ecologically important, especially in animals raised for feed production.

The recent ban of conventional cages within the EU has stimulated the development of large open farm buildings allowing egg production among free-ranging poultry as this alternative is regarded as the most ecologically friendly. Commercial egg production is commonly undertaken in large buildings where tens of thousands of egg-laying hens are housed. The activities of the hens will cause air pollution of respirable particulates (<4 μm diameter) as well as microorganisms beyond what was noted when cages were used. These particles will be inhaled causing an increase in the bioload defined as the level of biologically active components of the indoor ambient air which will require the immune system to be activated and as a consequence the energy consumption will increase and more feeding is required. When the free-ranging was introduced, it was noted that the feed conversion factor increased and it was thought to be a consequence of the poultry being more active as the indoor environment had been adapted to the new situation of farming with adequate floor space, lighting, ventilation and temperature control.

For their running or jumping performance, horses depend on their pulmonary function. It is known that frequent exposure to respiratory viral pathogens, strenuous exercise, long distance transport, and inhalation of harmful substances destroys various aspects of the pulmonary defense system and predispose performance horses to decreased performance.

The environmental factor on animal performance can also be illustrated accordingly; pigs reared in rooms that were cleaned before stocking grew 8% faster than pigs reared in rooms that were not cleaned. It has been shown that both the number of animals sharing an airspace, and the stocking density in terms of kg animal per cubic meter significantly affect the level of airborne particles, especially respirable dust particles. Thus, it is clear that the concentration of biologically active components in the indoor air—the bioload—will have an impact on animals' performance. It is not only the concentration of air borne particles but also the composition of these particles that are relevant. Mycotoxins have recently been identified as sub-micron size particles. Mycotoxines are some of the most biologically active components known causing an inflammatory response by activation of the immune system and any means to reduce the occurrence of mould and mycotoxins in the stable air would add to the reduction in the stable air bioload.

From the above follows a need to reduce the bioload of the stable air preferably through means of forcing the particles to settle on surfaces and at the same time increase the oxidative capacity of the stable air. Increased oxidation with reactive oxygen (superoxide) is the mechanism used by the immune system when combating potentially toxic compounds in the air through an inflammatory response. Such a response is not only restricted to the airways but will affect the performance of the animal and increase energy consumption. Fine particles in the air are positively charged and a negatively charged electrostatic field would not only serve as an efficient means to capture said particles forcing them to settle on surfaces with a lower electrostatic potential but in case the negatively charged electrostatic field is generated by enriching the air with electrons, the oxidative capacity of the air will also increase serving as an additional means to reduce the bioload of the ambient stable air.

BRIEF SUMMARY OF THE INVENTION

It is the primary object of the present invention to disclose a novel method to improve the yield of productive animals by optimizing the conversion of feedings to desirable agricultural products, enhancing growth and performance.

Another object of the invention is to disclose the method of improving the feed conversion factor.

These objects are obtained by this invention having been given the characterizing clauses mentioned in the claims.

The method according to the invention comprises generating a negatively charged electrostatic field extending throughout the building/space or sections thereof and in doing so an abundance of electron enriched air is generated.

State of the art technology is based on the generation of negatively charged air ions and associated precipitation of particles. The generation of an electrostatic field, according to this invention, of sufficient strength to capture particles requires the exposure of the electron emitting structure to the ambient air with nothing to interfere to disrupt said electrostatic field. Preferably, the whole emitting structure should have the same electrical charge as the coronal points of electron emission.

The arrangements of the present invention are a series of cables or bands consisting of a conductive material extended in the air of the animal housing on which carbon fibres are connected. Such multi stranded carbon fibres consist of >100 filaments, each serving as a point of release of electrons into the air (coronal points). These cables or bands are connected to a high voltage generator delivering a minimum of −6 kV at low amperage (less than 10 mA). The free-ending carbon fibre filaments will emit electrons, generating an negatively charged electrostatic field capturing the particles and at the same time causing oxygen molecules to become charged with an extra electron generating a superoxide molecule adding to the oxidative capacity of the ambient stable air.

The combination of a high voltage with low amperage makes the insulation of the emitter cables/bands from the surrounding structure critical. Any points of fixation of >0.5 mm width, such as a nylon thread, will have particulates attached to its surface and in combination with the naturally occurring air moisture, such points of fixation will with time become a conductor causing the loss of electrons from the emitter and the electrostatic field will no longer be generated.

Furthermore, the load of particulates may cause said particles to settle on the emitter and the free ending carbon fibres to the extent that the electron emitting capacity may be reduced. This risk needs to be handled by intermittently removing this aggregate of dust particles. This can be done by exerting of vibrating forces or impulses onto the carbon fibres. This is accomplished according to a need, that is from once a week in a horse stable or more in a poultry. The emitter band needs to withstand a cleaning from a high pressure water including vapour steam. Preferably the emitter bands/cables consists of non metallic material, but yet be electrical conductive.

Embodiments of the invention will now be described by way of examples with reference to the accompanying drawings, of which FIG. 1 is a side view of the electrostatic field generating arrangement.

Figure 1:
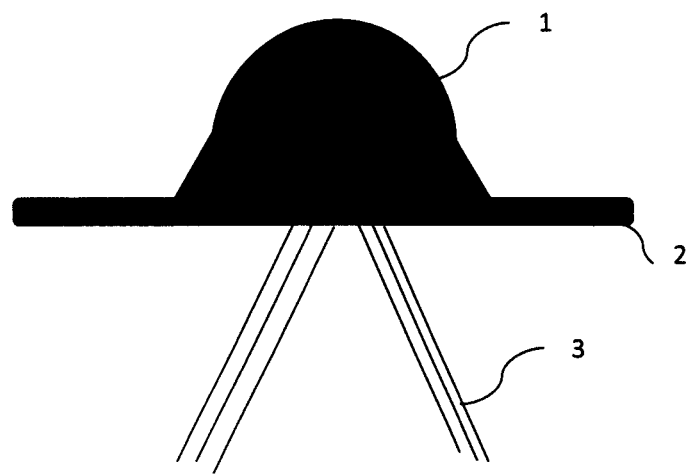
Figure 2:
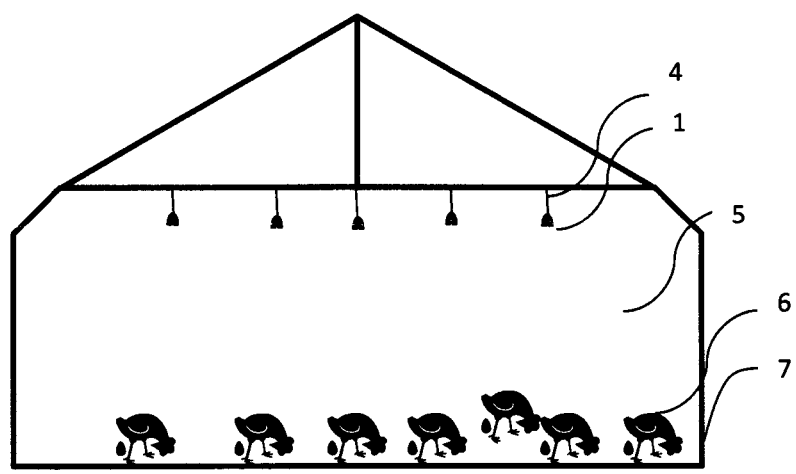
FIG. 2 shows the application of an air mounted system in an animal housing.
Figure 3:
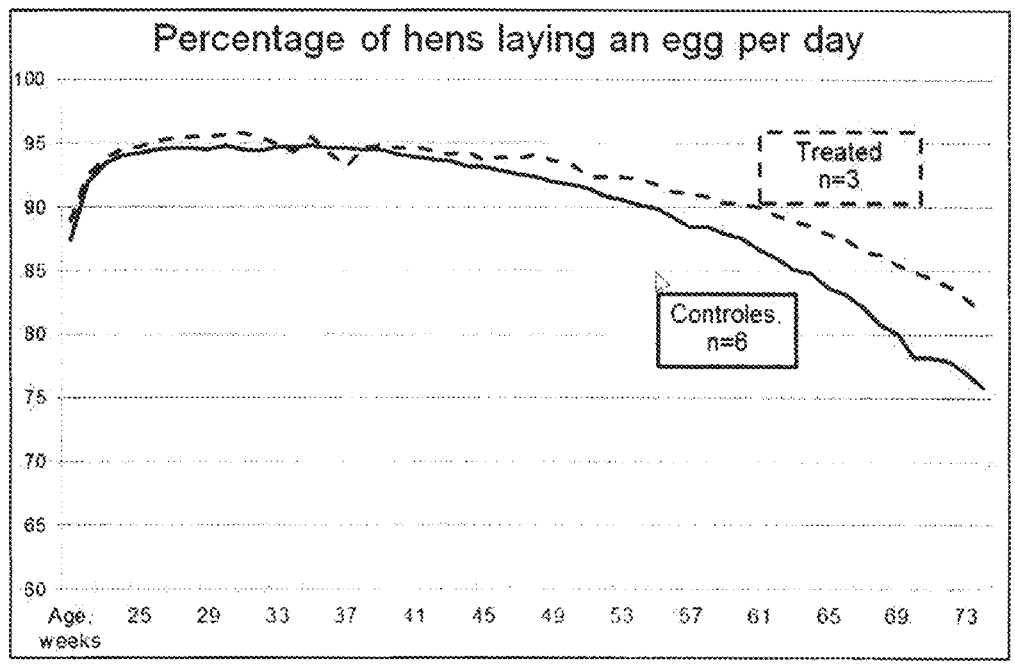
FIG. 3 depicts the percentage of days in which the hens are laying an egg.

In FIG. 1 the design of the emitter band is shown in a side view of the electrostatic field generating arrangement consisting of a semi-conductive polymer band 1 designed with a base 2 having a width of 10 to 25 mm, preferably 15 mm and on which carbon fibre filaments 3 are attached.

The basic conductive structure is charged with >6 kV. This charge will enable the release of electrons from the free ending carbon fibre filaments with one end attached to the conductive emitter band and the other extending out into the air and at the same time the conductive structure will become negatively charged serving as an electron emitting structure to generate a negatively charged electrostatic field.

FIG. 2 shows the application of an air mounted system in an animal housing with the electrostatic field generating arrangement 1 extended in the open stable air 5 by means of a thin, 0.2 to 1.0 mm, preferably 0.4 mm thick para-aramid thread 4, thus assisting in reducing the bioload of the stable air 5 and improving the productivity and performance of the animals 6 staying within the premises 7.

An industrial building with several 100 of $m^2$ of surface area and heavily polluted with particles and microorganisms such as a horse stable or egg production unit requires the electron emitting structure to be placed well away from the floor area. At the same time the electrostatic field has to have strength to enable the particles to be positioned on the floor (surface with zero electrostatic charge). This aspect of the invention is embodied in the form of an emitter design whereas high voltage (of more than minus 6 kV) at low amperage (<10 mA) is allowed to charge a band structure (see FIG. 1) consisting of a conductive core, preferably made from a conductive polymer of a sufficient strength to allow the electron emitting band to be hanging from the ceiling. The emitter band is connected to a high voltage generator and said voltage is presented to the thin carbon fibre filaments attached to the conductive band enabling the production of an electron enriched air with air cleaning properties related to enhanced oxidation and capturing of fine particles.

The positioning of the band structure over a long distance will require points of fixation. There is a considerable risk that the high voltage will force the electrons to deviate away from the emitter structure in case the points of fixation have any conductive capacity. Dirt and moisture positioned on a surface may provide a sufficiently conductive bridge to allow the electrons to be lost. As part of the embodiment of the innovation, the design of these fixation points has to be done with a thin (preferably 0.25-0.5 mm) and strong thread of low electrical conductivity. These requirements are meet by using spun para-aramid (Kevlar®) thread. These points of fixation will also allow the emitting band to vibrate when affected by a mechanical force, such as the one generated by the touch from the flying free ranging hens or by a strike from a rod. Furthermore, the stables are being cleaned using high pressure water, steam and disinfectant chemicals and the emitter has to withstand these conditions.

Example 1

Free Ranging Hens and Egg Production

The study data originates from four egg production units each of 20-30 000 free-ranging hens. Data on egg production and feed conversion were collected over nine egg production cycles in total, each covering the egg production starting at 22 weeks and finishing at 75 weeks of age of the poultry, approximately. During three of the egg production periods, the poultry housings were equipped with the preferred embodiment of the invention treating the ambient air.

FIG. 3 depicts the percentage of days in which the hens are laying an egg. The hatched line indicates averaged weekly data from those egg producing batches where the invention has been used and the solid line shows the same data for the six egg producing batches serving as controls. Statistically significant increase in the number of eggs produced was achieved from week 43 onwards.

During the period of significant change, i.e. weeks 41 to 75, the mean feed conversion factor improved from 2.26 to 2.01, (11.6%) with air treatment. It is of interest to note the significant increase in egg-laying percentage noted from week 43 as this would indicate that the influence of increasing age on animal performance is reduced. It is assumed that oxidative stress and increased immune system activity is involved in the ageing process. A potent mechanism for increased oxidative stress is the inhalation of fine and ultra-fine particles. Thus, a mechanism by which the level of oxidative stress is reduced would be beneficial for maintained productivity in high performance animals in particular.

The ability of the current invention of causing maintained productivity with improved feed conversion would strongly support a general mechanism of action requiring energy such as the level of activity of the immune system. Another observation made in support of this mechanism of action is the pattern of reactions observed in connection to vaccination. Although the hens had already been given the vaccine (Nobilis IB) prior to the introduction of electronic air cleaning (EAC) and should therefor be immune with no expected response, they responded to the combination of EAC and Nobilis IB vaccine with a marked reaction of reduced feed consumption and egg weight. Such a "primary" vaccine reaction was not noted in connection with subsequent vaccinations. It appears possible that the improved environment caused by the present invention enabled a physiological response to the vaccination based on a more optimal immune response in line with the appended claims.

Example 2

High Performance Horses

Other observations have been made in connection with horses where the current invention of electronic air cleaning has enabled the return to the Swedish National Show Jumping team of a 11 year old gelding (Arctic Aurora Borealis). This horse suffered from general fatigue and where at the brink of being taken out of competitions. The fatigue started in connection with a long distance transport from Sweden to Ireland in August 2008 and he did not respond to the standard treatment. Once his environment (stable, transporter and temporary stables) was exposed to the invention in March 2010, the appearance of mould in the stable air (FIG. 4) was markedly reduced and he improved his performance and in June, Arctic returned to the Swedish National show jumping team. At examination it was concluded that no longer did the immune cells (alveolar macrophages) in the bronchoalveolar lavage fluid show signs of being activated. It is known that frequent exposure to respiratory viral pathogens, strenuous exercise, long distance transport, and inhalation of harmful substances destroy various aspects of the pulmonary defense system and predispose performance horses to development of infectious and noninfectious respiratory disease.

Figure 4:
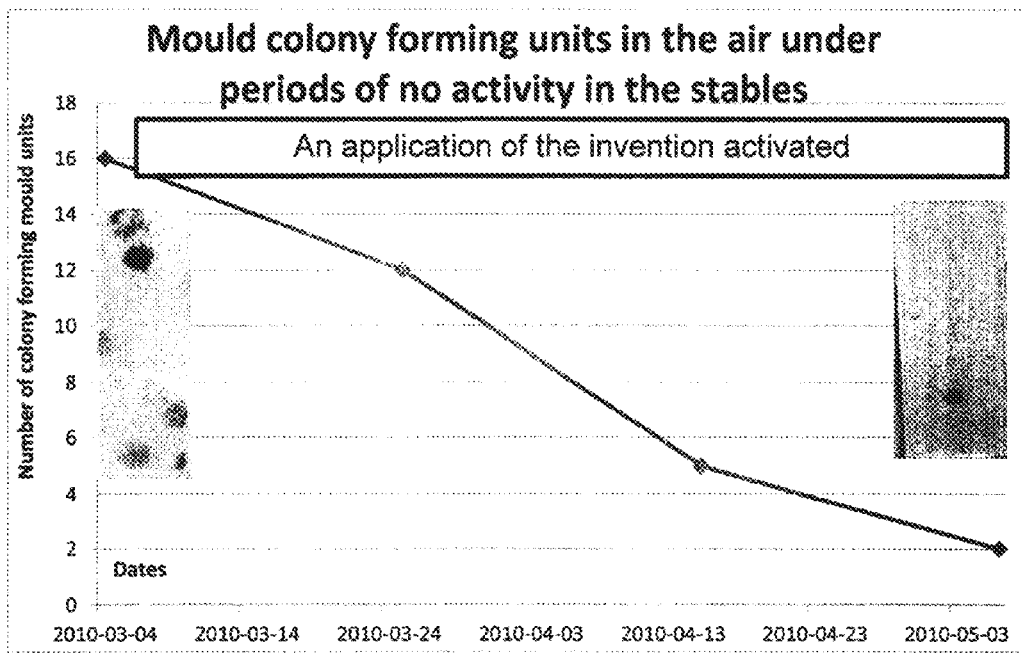
FIG. 4 shows the appearance of mould in the stable air.

FIG. 4 shows the reduction in mould colony forming units in the air of the stable of Arctic's as measured during 60 minutes exposure of the Hygicult® Y &F slide to the air.

The present invention is not intended to be limited to the foregoing example of egg production and performance horses, but encompass all such modifications that come under the scope of the appended claims. The most obvious additional applications are in the field of rapid growth, e.g. broilers and pigs.

Example 3

Fast Growing Pigs

The ability of the invention to improve pig production can be illustrated by data from 1350 pigs showing an increase in growth by 2.9% and a reduction in pulmonary infections from 0.8% to 0.13%. These data corroborates the findings from the egg production in that the reduced bioburden of the ambient air reduces the immunological stress caused by the indoor environment enabling an improved ability to manage endogenous bacteria in parallel to enhanced growth from better use of the nutritional energy.

The invention claimed is:

1. A method to improve an animal's biological or physical performance by reducing bioload, defined as biologically active particles in air of a stable or in the air within transporter vehicles, the method comprising:
   generating a negatively charged electrostatic field operating within a room by capturing said particles using high voltage >6 kV at low amperage (<10 mA) applied to a polymer conductive band (1) positioned in the air (5) of the stable or the transporter vehicle,
   wherein carbon fiber filaments (3) are attached to the polymer conductive band, and
   wherein the high voltage >6 kV at low amperage (<10 mA) applied to a polymer conductive band (1) causes a release of electrons from a free end of the carbon fiber filaments (3) into the air, thereby generating the negatively charged electrostatic field.

2. An arrangement to improve biological or physical performance by reducing bioload, defined as biologically active particles in air of a stable or the air within transporter vehicles, the arrangement comprising:
   means for producing a negatively charged electrostatic field capturing air borne particulate matter whereby high voltage >6 kV at low amperage (<10 mA) is applied to a conducting polymer band (1) positioned in the air (5) of the stable or the transporter vehicle,
   wherein carbon fiber filaments (3) are attached to the polymer conductive band, and
   wherein the high voltage >6 kV at low amperage (<10 mA) being applied to a polymer conductive band (1) causes a release of electrons from a free end of the carbon fiber filaments (3) into the air, thereby generating the negatively charged electrostatic field.

3. Arrangement according to claim 2, further comprising paraaramid threads (4) that extend from the polymer conductive band (1) and define a point of fixation of the polymer conductive band (1) to the room, the paraaramid threads (4) being 0.2 to 1.0 mm thick.

4. Arrangement according to claim 3, wherein said points of fixation are secured and will allow the polymer conductive band to be vibrated when effected mechanically.

5. Arrangement according to claim 2, wherein the polymer conductive band is positioned in ambient indoor air extending throughout a building structure.

6. Arrangement according to claim 3, wherein the polymer conductive band is positioned in the ambient indoor air extending throughout the building structure.

7. Arrangement according to claim 4, wherein the basic conductive band is positioned in ambient indoor air extending throughout the building structure.

* * * * *